United States Patent
Dekany et al.

(10) Patent No.: US 10,364,449 B2
(45) Date of Patent: Jul. 30, 2019

(54) FERMENTATIVE PRODUCTION OF OLIGOSACCHARIDES

(71) Applicant: Glycom A/S, Hørsholm (DK)

(72) Inventors: Gyula Dekany, Sinnamon Park (AU);
Pauline Peltier-Pain, Orleans (FR);
Dóra Molnár-Gábor, Budapest (HU);
Markus Jondelius Hederos, Trelleborg (SE)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 14/914,520

(22) PCT Filed: Sep. 5, 2014

(86) PCT No.: PCT/DK2014/050273
§ 371 (c)(1),
(2) Date: Feb. 25, 2016

(87) PCT Pub. No.: WO2015/032413
PCT Pub. Date: Mar. 12, 2015

(65) Prior Publication Data
US 2016/0215315 A1    Jul. 28, 2016

(30) Foreign Application Priority Data
Sep. 6, 2013 (DK) .................. 2013 70497

(51) Int. Cl.
| | |
|---|---|
| C12P 19/18 | (2006.01) |
| C07H 3/06 | (2006.01) |
| C12P 19/26 | (2006.01) |
| C08B 37/00 | (2006.01) |
| C12P 19/00 | (2006.01) |

(52) U.S. Cl.
CPC ............. *C12P 19/18* (2013.01); *C07H 3/06* (2013.01); *C08B 37/006* (2013.01); *C12P 19/00* (2013.01); *C12P 19/26* (2013.01); *C12Y 204/01065* (2013.01); *C12Y 204/01087* (2013.01); *C12Y 204/01099* (2013.01)

(58) Field of Classification Search
CPC ........... C12P 19/14; C12P 19/04; C12P 19/18; C12P 19/12; C12P 19/00; C12P 19/26; C12P 19/44; C12P 19/28; C12P 19/60; C12P 19/64
See application file for complete search history.

(56) References Cited

U.S. PATENT DOCUMENTS

| | | |
|---|---|---|
| 2002/0025560 A1 | 2/2002 | Koizumi et al. |
| 2012/0208181 A1 | 8/2012 | Merighi et al. |

FOREIGN PATENT DOCUMENTS

| | | |
|---|---|---|
| EP | 1426441 | 6/2004 |
| WO | WO0104341 | 1/2001 |
| WO | 2007101862 A1 | 9/2007 |
| WO | WO2010070104 | 6/2010 |
| WO | WO2011100979 | 8/2011 |
| WO | WO2011100980 | 8/2011 |
| WO | WO2012007585 | 1/2012 |
| WO | WO2012007588 | 1/2012 |
| WO | WO2012113405 | 8/2012 |
| WO | WO2012127410 | 9/2012 |
| WO | WO2012155916 | 11/2012 |
| WO | WO2012156897 | 11/2012 |
| WO | WO2012156898 | 11/2012 |
| WO | WO2012168495 | 12/2012 |
| WO | WO2013044928 | 4/2013 |
| WO | WO2013091660 | 6/2013 |

OTHER PUBLICATIONS

"Glycosyltransferases: Tools for Synthesis andModification of Glycans" Biofiles 2.1, 2, retrieved from http://www.sigmaaldrich.com/technical-documents/articles/biofiles/glycosyltransferases.html on Nov. 6, 2017 (Year: 2007).*
Han, N. et al, "Biotechnological production of human milk oligosaccharides", Biotechnology Advances, vol. 30, pp. 1268-1278, (2012).
Duman, C. et al, "In vivo fucosylation of lacto-N-neotetraose and lacto-N-neohexaose by heterologous expression of helocobacter pylori alpha-1,3 fucosyltransferase in engineered *Escherichia coli*", Glycoconjugate J., vol. 18, pp. 465-474, (2001).
Duman, C. et al, "Assessment of the two Helicobacter pylori alpha-1,3-Fucosyltransferase ortholog genes for the large-scale synthesis of LewisX human milk oligosaccharides by metobolically engineered *Escherichia coli*", Biotechnol. Prog., vol. 20, pp. 412-419, (2004).
Antoine, T. et al, "Large scale in vivo synthesis of globotriose and globotetraose by high cell density culture of metabolically engineered *Escherichia coli*", Biochimie, vol. 87, pp. 197-203, (2005).
Randriantsoa, M et al, "Synthesis of globopentaose using a novel beta1,3-galactosyltransferase activity of the Haemophilus influenzae Beta1,3-N-acetylgalactosaminyltransferase LgtD", FEBS Letters vol. 581, pp. 2652-2656, (2007).

(Continued)

*Primary Examiner* — Rebecca E Prouty
(74) *Attorney, Agent, or Firm* — Neal, Gerber & Eisenberg LLP

(57) ABSTRACT

The application discloses a method for producing an oligosaccharide of at least four monosaccharide units, advantageously an HMO, particularly an HMO of only four monosaccharide units, said method comprising a step of: culturing, in a culture medium containing a fucosylated, sialylated or N-acetyl-glucosaminylated lactose trisaccharide as acceptor, a genetically modified cell having a recombinant gene that encodes an enzyme capable of modifying said acceptor or one of the necessary intermediates in the biosynthetic pathway of the oligosaccharide of at least four monosaccharide units, advantageously an HMO, particularly an HMO of only four monosaccharide units, from said acceptor.

10 Claims, No Drawings

(56) References Cited

OTHER PUBLICATIONS

Freeze, H. et al, Glycosylation precursors, in: Essentials of Glycobiology, 2nd edition (Eds. A. Varki et al.), Cold Spring Harbour Laboratory Press, Chapter 4, (2009).

Drouillard, S. et al, "Large-scale synthesis of H-antigen oligosaccharides by expressing helicobacter pylori alpha1,2-Fucosyltransferase in metabolically engineered *Escherichia coli* cells", Angew. Chem. Int. Ed., vol. 45, pp. 1778-1780, (2006).

Samain, E. et al, "Production of 0-acetylated and sulfated chitooligosaccharides by recombinant *Escherichia coli* strains harboring different combinations of nod genes", J. Biotechnology, vol. 72, pp. 33-47, (1999).

Ishizuka, Y. et al, "Three-dimensional structure of Fucosyllactoses in an aqueous solution", J. Carbohydrate Chemistry, 18:5:523-533, DOI: 10.1080/07328309908544016, (1999).

Priem, B. et al, "A new fermentation process allows large-scale production of human milk oligosaccharides by metabolically engineered bacteria", Glycobiology, 12:4:235-240, (2002).

Murata, T. et al, "Facile enzymatic conversion of lactose into lacto-N-tetratose and lacto-N-neotetratose", Glycoconjugate J., vol. 16, pp. 189-195, (1999).

Albermann, C. et al, "Synthesis of the milk oligosaccharide 2'fucosyl-lactose using recombinant bacterial enzymes", Carbohydrate Research, vol. 334, pp. 97-103, (2001).

Becker, D.J. et al., "Fucose: biosynthesis and biological function in mammals," Glycobiology, 2003, vol. 13 (7), pp. 41R-53R.

Arteaga-Cabello, J., et al. (2011). "Synthesis of 2-FL and LDFT by metabolically engineered *E. coli* through the fkp gene from Bacteroides fragilis." Annual Conference of the Society for Glycobiology, p. 1499.

\* cited by examiner

FERMENTATIVE PRODUCTION OF OLIGOSACCHARIDES

CROSS REFERENCE TO RELATED APPLICATIONS

This is a national stage filing in accordance with 35 U.S.C. § 371 of PCT/DK2014/050273, filed Sep. 5, 2014, which claims the benefit of the priority of Denmark Patent Application PA 2013 70497, filed Sep. 6, 2013, the contents of each are incorporated herein by reference.

FIELD OF THE INVENTION

The present invention relates to a method of making complex oligosaccharides, particularly human milk oligosaccharides (HMOs), by whole cell biosynthesis.

BACKGROUND OF THE INVENTION

In recent years, the interest in manufacturing and commercializing complex oligosaccharides including secreted oligosaccharides has increased significantly due to the roles of these compounds in numerous biological processes in living organisms. Secreted oligosaccharides such as human milk oligosaccharides (HMOs), mucin oligosaccharides and Lewis type oligosaccharides have become important potential products for nutrition and therapeutic uses. As a result, low cost ways of producing industrially these oligosaccharides, particularly HMOs, have been sought.

To date, the structures of at least 115 HMOs have been determined (see Urashima et al.: *Milk Oligosaccharides*, Nova Biomedical Books, New York, 2011, ISBN: 978-1-61122-831-1), and considerably more are probably present in human milk. The thirteen core structures identified to date, for the 115 HMOs, are listed in Table 1.

TABLE 1

| | Core HMO structures | |
|---|---|---|
| No | Core name | Core structure |
| 1 | lactose (Lac) | Galβ1-4Glc |
| 2 | lacto-N-tetraose (LNT) | Galβ1-3GlcNAcβ1-3Galβ1-4Glc |
| 3 | lacto-N-neotetraose (LNnT) | Galβ1-4GlcNAcβ1-3Galβ1-4Glc |
| 4 | lacto-N-hexaose (LNH) | Galβ1-3GlcNAcβ1-3(Galβ1-4GlcNAcβ1-6)Galβ1-4Glc |
| 5 | lacto-N-neohexaose (LNnH) | Galβ1-4GlcNAcβ1-3(Galβ1-4GlcNAcβ1-6)Galβ1-4Glc |
| 6 | para-lacto-N-hexaose (para-LNH) | Galβ1-3GlcNAcβ1-3Galβ1-4GlcNAcβ1-3Galβ1-4Glc |
| 7 | para-lacto-N-neohexaose (para-LNnH) | Galβ1-4GlcNAcβ1-3Galβ1-4GlcNAcβ1-3Galβ1-4Glc |
| 8 | lacto-N-octaose (LNO) | Galβ1-3GlcNAcβ1-3(Galβ1-4GlcNAcβ1-3Galβ1-4GlcNAcβ1-6)Galβ1-4Glc |
| 9 | lacto-N-neooctaose (LNnO) | Galβ1-4GlcNAcβ1-3(Galβ1-3GlcNAcβ1-3Galβ1-4GlcNAcβ1-6)Galβ1-4Glc |
| 10 | iso-lacto-N-octaose (iso-LNO) | Galβ1-3GlcNAcβ1-3(Galβ1-3GlcNAcβ1-3Galβ1-4GlcNAcβ1-6)Galβ1-4Glc |
| 11 | para-lacto-N-octaose (para-LNO) | Galβ1-3GlcNAcβ1-3Galβ1-4GlcNAcβ1-4GlcNAcβ1-3Galβ1-4Glc |
| 12 | lacto-N-neodecaose (LNnD) | Galβ1-3GlcNAcβ1-3[Galβ1-4GlcNAcβ1-3(Galβ1-4GlcNAcβ1-6)Galβ1-4GlcNAcβ1-6]Galβ1-4Glc |
| 13 | lacto-N-decaose (LND) | Galβ1-3GlcNAcβ1-3[Galβ1-3GlcNAcβ1-3(Galβ1-4GlcNAcβ1-6)Galβ1-4GlcNAcβ1-6]Galβ1-4Glc |

A few HMOs have recently been synthesized, for example, by hydrogenating their benzyl glycoside precursors after removing other protecting groups from such precursors and then isolating (e.g. by crystallization) the HMOs (WO 2011/100979, WO 2011/100980, WO 2012/007585, WO 2012/007588, WO 2012/113405, WO 2012/127410, WO 2012/155916, WO 2012/156897, WO 2012/156898, WO 2013/044928, WO 2013/091660).

Direct fermentative production of HMOs, especially of short chain trisaccharides, has recently become practical (see Han et al. *Biotechnol. Adv.* 30, 1268 (2012) and references cited therein). Such fermentation technology has used a recombinant *E. coli* system wherein one or more types of glycosyl transferases originating from viruses or bacteria have been co-expressed to glycosylate exogenously added lactose, which has been internalized by the LacY permease of the *E. coli*. However, the use of more than one type of glycosyl transferase for the production of oligosaccharides of four or more monosaccharide units, like LNnT or fucosylated LNnT, has always led to the formation of a complex mixture of oligosaccharides. This is believed to have been due to the overglycosylation of the diverse intermediates produced from the lactose feed as a result of different relative activities of the different glycosyl transferases (WO 01/04341, Dumon et al. *Glycoconj. J.* 18, 465 (2001), Priem et al. *Glycobiology* 12, 235 (2002), Dumon et al. *Biotechnol. Prog.* 20, 412 (2004), M. Randriantsoa: *Synthèse microbiologique des antigènes glucidiques des groupes sanguins*, Thèse de Doctorat soutenue le Sep. 30, 2008 a l'Université Joseph Fourier, Grenoble, France).

An alternative fermentation method has involved the use of a recombinant *E. coli* expressing a β-1,3-GalNAc transferase for glycosylating a trisaccharide, globotriose to make globotetraose or globopentaose (Antoine et al. *Biochimie* 87, 197 (2005), Randriantsoa et al. *FEBS Letters* 581, 2652 (2007)).

However, there has been a continuing need for an efficient method of making fucosylated, sialylated and N-acetyl-glucosaminylated oligosaccharides, particularly HMOs, of four or more monosaccharide units.

SUMMARY OF THE INVENTION

The invention relates to a method for producing an oligosaccharide of at least four monosaccharide units, advantageously an HMO, particularly an HMO of only four monosaccharide units, said method comprising a step of:
  culturing, in a culture medium containing a fucosylated, sialylated or N-acetyl-glucosaminylated lactose trisaccharide as acceptor, a genetically modified cell having a recombinant gene that encodes an enzyme capable of modifying said acceptor or one of the necessary intermediates in the biosynthetic pathway of the oligosaccharide of at least four monosaccharide units, advantageously an HMO, particularly an HMO of only four monosaccharide units, from said acceptor.

Advantageously, said HMO is selected from difucosyllactose, sialyl-fucosyllactose, LNT and LNnT and said acceptor is selected from 2'-FL, 3-FL, 3'-SL and lacto-N-triose.

Also advantageously, said enzyme encoded by said recombinant gene is a glycosyl transferase selected from β-1,3-galactosyl transferase, β-1,4-galactosyl transferase, α-1,2-fucosyl transferase, α-1,3-fucosyl transferase and α-2,3-sialyl transferase.

Optionally, said fucosylated, sialylated or N-acetyl-glucosaminylated lactose trisaccharides are made by a method comprising the initial steps of:
culturing, in an initial culture medium containing lactose as an initial acceptor, a initial genetically modified cell having an recombinant gene that encodes a β-1,3-N-acetyl-glucosaminyl transferase capable of N-acetyl-glucosaminylating said lactose initial acceptor, or α-1,2- or α-1,3-fucosyl transferase capable of fucosylating said lactose initial acceptor, or α-2,3-sialyl transferase capable of sialylating said lactose initial acceptor, and
separating said fucosylated, sialylated or N-acetyl-glucosaminylated lactose trisaccharide, advantageously lacto-N-triose, 2'-FL, 3-FL or 3'-SL, from said initial cell, from said initial culture medium or advantageously from both.

DETAILED DESCRIPTION OF THE INVENTION

In accordance with this invention, it has been surprisingly discovered that an exogenous fucosylated, sialylated or N-acetyl-glucosaminylated lactose acceptor can be successfully internalized into a genetically modified cell and then glycosylated by the cell to make a glycosylated fucosyl, sialyl or N-acetyl-glucosaminyl lactose, especially an HMO having at least four monosaccharide units, preferably only four monosaccharide units.

In this invention, the term "genetically modified cell" preferably means a cell in which at least one DNA sequence has been added to, deleted from or changed in its genome, so that the cell has a changed phenotype. This change in phenotype alters the characteristics of the genetically modified cell from that of the wild type cell. Thus, the genetically modified cell can perform at least an additional chemical transformation, when cultured or fermented, due to the added or changed DNA that encodes the expression of at least one enzyme not found in the wild type cell, or the genetically modified cell cannot perform a chemical transformation due to the deleted, added or changed DNA that encodes the expression of an enzyme found in the wild type cell. The genetically modified cell can be produced by well-known, conventional genetic engineering techniques. The genetically modified cell can be bacteria or a yeast but preferably is a *bacterium*. Preferred bacteria include *Escherichia coli, Bacillus* spp. (e.g. *Bacillus subtilis*), *Campylobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae, Neisseria meningitis, Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, particularly *E. coli*.

Also in this invention, the term "oligosaccharide" preferably means a sugar polymer containing at least three monosaccharide units, i.e. a tri-, tetra- or higher oligosaccharide. The oligosaccharide can have a linear or branched structure containing monosaccharide units that are linked to each other by interglycosidic linkages. Particularly, the oligosaccharide comprises a lactose residue at the reducing end and one or more naturally occurring monosaccharides of 5-9 carbon atoms selected from aldoses (e.g. glucose, galactose, ribose, arabinose, xylose, etc.), ketoses (e.g. fructose, sorbose, tagatose, etc.), deoxysugars (e.g. rhamnose, fucose, etc.), deoxy-aminosugars (e.g. N-acetyl-glucosamine, N-acetyl-mannosamine, N-acetyl-galactosamine, etc.), uronic acids and ketoaldonic acids (e.g. sialic acid). Preferably, the oligosaccharide is an HMO.

In carrying out the method of this invention for making a glycosylated fucosyl, sialyl or N-acetyl-glucosaminyl lactose, especially an HMO of at least four monosaccharide units, a genetically modified final cell having a recombinant gene that encodes an enzyme capable of modifying an exogenous fucosyl, sialyl or N-acetyl-glucosaminyl lactose trisaccharide acceptor or a necessary intermediate in the biosynthetic pathway of the oligosaccharide from said acceptor is cultured in a culture medium containing the acceptor. The genetically modified cell used in the method of this invention comprises one or more endogenous or recombinant genes encoding one or more glycosyl transferase enzymes that are able to transfer the glycosyl residue of an activated sugar nucleotide to an internalized acceptor molecule. The gene or an equivalent DNA sequence thereof, if it is recombinant, is introduced into the cell by known techniques, using an expression vector. The origin of the heterologous nucleic acid sequence can be any animal (including human) or plant, eukaryotic cells such as those from *Saccharomyces cerevisae, Saccharomyces pombe, Candida albicans* and the like, prokaryotic cells such as those originated from *E. coli, Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitis*, or virus. The glycosyl transferase enzyme expressed by the protein encoded by the gene or equivalent DNA sequence can be a glucosyl transferase, galactosyl transferase, N-acetylglucosaminyl transferase, N-acetylgalactosaminyl transferase, glucuronosyl transferase, xylosyl transferase, mannosyl transferase, fucosyl transferase, sialyl transferase or the like. In a preferred embodiment, the glycosyl transferase is selected from the group consisting of β-1,3-N-acetylglucosaminyl transferase, β-1,3-galactosyl transferase, acetylgalactosaminyl transferase, β-1,3-glucuronosyl transferase, β-1,6-N-acetylglucosaminyl transferase, β-1,4-N-acetylgalactosaminyl transferase, β-1,4-galactosyl transferase, α-1,3-galactosyl transferase, α-1,4-galactosyl transferase, α-2,3-sialyl transferase, α-2,6-sialyl transferase, α-2,8-sialyl transferase, α-1,2-fucosyl transferase, α-1,3-fucosyl transferase and α-1,4-fucosyl transferase. More preferably, the glycosyl transferase is selected from the group of enzymes involved in making HMO core structures nos. 2-13 shown in Table 1, and fucosylated and/or sialylated HMOs, that is β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and/or α-1,4 fucosyl transferase. The genes encoding the above-mentioned transferases have been described in the literature.

When carrying out the method of this invention, a glycosyl transferase mediated glycosylation reaction preferably takes place in which an activated sugar nucleotide serves as donor. An activated sugar nucleotide generally has a phosphorylated glycosyl residue attached to a nucleoside, a specific glycosyl transferase enzyme accept only a specific sugar nucleotide. Thus, preferably the following activated sugar nucleotides are involved in the glycosyl transfer: UDP-Glc, UDP-Gal, UDP-GlcNAc, UDP-GalNAc, UDP-glucuronic acid, GDP-Fuc and CMP-sialic acid, particularly those selected from the group consisting of UDP-Gal, UDP-GlcNAc, GDP-Fuc and CMP-sialic acid.

In one embodiment of the method, the genetically modified cell is able to produce one or more activated sugar nucleotide mentioned above by a de novo pathway. In this regard, an activated sugar nucleotide is made by the cell under the action of enzymes involved in the de novo biosynthetic pathway of that respective sugar nucleotide in a stepwise reaction sequence starting from a simple carbon source like glycerol, fructose or glucose (for a review for monosaccharide metabolism see e.g. H. H. Freeze and A. D. Elbein: *Chapter* 4: *Glycosylation precursors*, in: Essentials of Glycobiology, $2^{nd}$ edition (Eds. A. Varki et al.), Cold Spring Harbour Laboratory Press (2009)). The enzymes involved in the de novo biosynthetic pathway of an activated sugar nucleotide can be naturally present in the cell or introduced into the cell by means of gene technology or recombinant DNA techniques, all of them are parts of the general knowledge of the skilled person.

In another embodiment, the genetically modified cell can utilize salvaged monosaccharide for producing activated sugar nucleotide. In the salvage pathway, monosaccharides derived from degraded oligosaccharides are phosphorylated by kinases, and converted to nucleotide sugars by pyrophosphorylases. The enzymes involved in the procedure can be heterologous ones, or native ones of the cell used for genetic modification. Preferably, the synthesis of GDP-fucose or CMP-sialic acid can be accomplished using the salvage pathway, when exogenous fucose or sialic acid is also added to the culture.

It should be emphasized, that whatever way, either the de novo, or the salvage pathway taken for producing activated sugar nucleotides by the genetically modified cell is advantageous compared to in vitro versions of transfer glycosylation, as it avoids using the very expensive sugar nucleotide type donors added exogenously, hence the donors are formed by the cell in situ and the phosphatidyl nucleoside leaving groups are recycled in the cell.

According to the preferred embodiment disclosed above, the genetically modified cell is cultured in the presence of a carbon-based substrate such as glycerol, glucose, glycogene, fructose, maltose, starch, cellulose, pectin, chitin, sucrose etc., to internalize the acceptor added in the cell where the glycosylation takes place. Preferably, the cell is cultured on glycerol and/or glucose and/or fructose.

The method of the invention also involves initially transporting an exogenous fucosyl, sialyl or N-acetyl-glucosaminyl lactose trisaccharide, as an acceptor molecule, from the culture medium into the genetically modified cell for glycosylation where it can be glycosylated to produce higher oligosaccharides. The acceptor can be added exogenously in a conventional manner to the culture medium, from which it can then be transported into the cell. The internalization of the acceptor should not, of course, affect the basic and vital functions or destroy the integrity of the cell. In one embodiment the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In other embodiment the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards galactose and simple galactosyl disaccharides like lactose. The specificity of a transporter protein or permease towards the sugar moiety of the substrate to be internalized can be altered by mutation by means of known recombinant DNA techniques. In a preferred embodiment the internalization of the exogenous lactose derivative acceptor takes place via an active transport mechanism.

The method of the invention is characterized also in that the genetically modified cell lacks enzymatic activity liable to degrade the precursor fucosyl, sialyl or N-acetyl-glucosaminyl lactose, the product glycosylated fucosyl, sialyl or N-acetyl-glucosaminyl lactose, especially an HMO having at least four monosaccharide units, and the metabolic intermediates towards the final products.

Culturing or fermenting the genetically modified cell according to the method of this invention can be carried out in a conventional manner. When cultured, the exogenous fucosyl, sialyl or N-acetyl-glucosaminyl lactose trisaccharide is internalized into, and accumulates in, the genetically modified cell. The internalized substrate, acting as acceptor, participates in a glycosyl transferase induced glycosylation reaction, in which a glycosyl residue of an activated nucleotide donor is transferred so that the acceptor is glycosylated giving thus a glycosylated fucosyl, sialyl or N-acetyl-glucosaminyl lactose tetrasaccharide. Optionally, when more than one glycosyl transferase is expressed by the cell, additional glycosylation reactions can occur resulting in the formation of penta- or higher oligosaccharide derivatives. Of course, the cell preferably lacks any enzyme activity which would degrade the acceptor or the oligosaccharides produced in the cell. Preferably, the culturing comprises (a) a first phase of exponential cell growth ensured by a carbon-based substrate, and (b) a second phase of cell growth limited by a carbon-based substrate which is added continuously.

At the end of culturing, the oligosaccharide as product can be accumulated both in the intra- and the extracellular matrix. The product can be transported to the supernatant in a passive way, i.e. it diffuses outside across the cell membrane. The transport can be facilitated by sugar efflux transporters, proteins that promote the effluence of sugar derivatives from the cell to the supernatant. The sugar efflux transporter can be present exogenously or endogenously and is overexpressed under the conditions of the fermentation to enhance the export of the oligosaccharide derivative produced. The specificity towards the sugar moiety of the product to be secreted can be altered by mutation by means of known recombinant DNA techniques.

According to a preferred embodiment, the method also comprises the addition of an inducer to the culture medium. The role of the inducer is to promote the expression of enzymes involved in the de novo or salvage pathway and/or of permeases involved in the active transport and/or of sugar efflux transporters of the cell. Preferably, the inducer is isopropyl β-D-thiogalactoside (IPTG).

After carrying out the method of this invention, the glycosylated fucosyl, sialyl or N-acetyl-glucosaminyl lactose tetrasaccharide, preferably an HMO of at least four monosaccharide units formed can be collected from the culture or fermentation broth in a conventional manner. The supernatant containing the oligosaccharide can be separated from the cells by centrifugation. The separated cells can be resuspended in water and subjected to heat and/or acid treatment in order to permeabilize them for releasing the oligosaccharide glycoside accumulated intracellularly. The product can be separated from the treated cell by centrifugation. The two supernatants containing the extra- and intracellular products, respectively, are combined and the products can be purified and isolated by means of standard separation, purification and isolation techniques such as gel and/or cationic ion exchange resin (H+ form) chromatography. Preferably, the oligosaccharide derivative is collected only from the supernatant.

The fucosylated, sialylated or N-acetyl-glucosaminylated lactose as acceptor used in this invention is preferably a reducing trisaccharide moiety of a HMO. In this regard, a preferred trisaccharide is lacto-N-triose (GlcNAcβ-3Galβ1-4Glc), a common moiety of core HMO structures nos. 2-13 in Table 1. Moreover, other preferred trisaccharide acceptors are 2'-FL, 3-FL and 3'-SL, which can serve as precursors for non-GlcNAc-containing HMO tetrasaccharides.

In accordance with this invention, an HMO having at least four monosaccharide units can be produced by fermenting a genetically modified cell starting with an internalized exogenous trisaccharide precursor selected from lacto-N-triose, 2'-FL, 3-FL and 3'-SL, the method comprises the steps of:
  (i) obtaining a LacZ$^-$Y$^+$ E. coli cell that comprises at least one recombinant gene encoding an enzyme capable of performing a glycosylation by means of, preferably exogenous, glycosyl transferases on the exogenous precursor or one of the intermediates in the biosynthetic pathway of an HMO having at least four monosaccharide units from the exogenous precursor necessary for the synthesis of the HMO having at least four monosaccharide units from the exogenous precursor, and also the components for expressing the gene in the cell; and
  (ii) culturing the cell on a carbon-based substrate in the presence of said exogenous precursor, under conditions inducing the internalization of said exogenous precursor by the cell and the production of an HMO having at least four monosaccharide units by the cell.

Preferred glycosyl transferases are selected from β-1,3-galactosyl transferase, β-1,4-galactosyl transferase, α-1,2-fucosyl transferase, α-1,3-fucosyl transferase and α-2,3-sialyl transferase.

Preferably, the Lac Z$^-$Y$^+$ E. coli cell is cultured in the following way:
  (a) a first phase of exponential cell growth ensured by a carbon-based substrate, and
  (b) a second phase of cell growth limited by a carbon-based substrate which is added continuously.

Also preferably, said carbon-based substrate is selected from the group consisting of glycerol and glucose. More preferably, the carbon-based substrate added during the second phase glycerol.

Also preferably, said culturing is performed under conditions allowing the production of a culture with a high cell density.

Optionally, said culturing further comprises a third phase of slowed cell growth obtained by continuously adding to the culture an amount of said carbon-based substrate that is less than the amount of the carbon-based substrate added in said second phase so as to increase the content of the oligosaccharide produced in the high cell density culture.

Also preferably, the amount of the carbon-based substrate added continuously to the cell culture during said third phase is at least 30% less than the amount of the carbon-based substrate added continuously during said second phase.

Also preferably, the method further comprises the addition of an inducer to said culture medium to induce the expression in said cell of said enzyme and/or of a protein involved in said transport. The inducer is preferably isopropyl β-D-thiogalactoside (IPTG).

The exogenous trisaccharide to be internalized by and glycosylated in the fermented cell can be added to the culture medium at once or continuously. If added at once, it is done at the end of the first phase of exponential cell growth. To avoid overflow metabolism and other side processes during the fermentation, the exogenous acceptor is dissolved in the feeding solution to be added during the second (and optionally the third) phase, therefore a continuous addition of the acceptor (with the carbon-based substrate) is realized.

Also preferably, the method is able to produce a human milk oligosaccharide selected from the group consisting of difucosyllactose, sialyl-fucosyl lactose, LNT, LNnT, sialylated and/or fucosylated LNT and sialylated and/or fucosylated LNnT. The resulting HMO, after fermentation, can be isolated in a conventional manner from the aqueous fermentation broth, in which the LacZ$^-$Y$^+$ E. coli cell was cultured. Preferably, the aqueous fermentation broth is preferably separated (for example, by centrifugation) from the fermented E. coli, cells, filtered and then contacted with cationic and anionic ion exchange resins to remove proteins and ionic compounds. The resulting aqueous medium can then be dried (for example, by freeze drying).

An embodiment of the invention relates to making difucosyllactose comprising:
  (i) obtaining a genetically modified E. coli cell that comprises a recombinant gene encoding an α-1,2-fucosyl transferase; and
  (ii) culturing said cell on a carbon-based substrate in the presence of exogenous 2'-FL under conditions inducing its internalization by the cell and the production of difucosyllactose by the cell.

Preferably, 2'-FL used as exogenous acceptor in the fermentation process is made in an initial fermentation comprising the steps:
  culturing, in an initial culture medium containing exogenously added lactose as initial acceptor, an initial genetically modified cell, preferably E. coli, having a recombinant gene that encodes an α-1,2-fucosyl transferase capable of fucosylating lactose, and
  separating 2'-FL from said initial cell, from said initial culture medium or from both.

In the two separate fermentation processes preferably the same genetically modified cell is used.

According to the another embodiment, difucosyllactose can be produced in an alternative way comprising:
  (i) obtaining a genetically modified E. coli cell that comprises a recombinant gene encoding an α-1,3-fucosyl transferase; and
  (ii) culturing said cell on a carbon-based substrate in the presence of exogenous 2'-FL under conditions inducing its internalization by the cell and the production of difucosyllactose by the cell.

Preferably, 2'-FL used as exogenous acceptor in the fermentation process is made in an initial fermentation comprising the steps:
  culturing, in an initial culture medium containing exogenously added lactose as acceptor, an initial genetically modified cell, preferably E. coli, having a recombinant gene that encodes an α-1,2-fucosyl transferase capable of fucosylating lactose, and separating 2'-FL from said initial cell, from said initial culture medium or from both.

According to a further embodiment in making difucosyllactose, the method comprises:
(i) obtaining a genetically modified *E. coli* cell that comprises a recombinant gene encoding an α-1,2-fucosyl transferase; and
(ii) culturing said cell on a carbon-based substrate in the presence of exogenous 3-FL under conditions inducing its internalization by the cell and the production of difucosyllactose by the cell.

Preferably, 3-FL used as exogenous acceptor in the fermentation process is made in an initial fermentation comprising the steps:
culturing, in an initial culture medium containing exogenously added lactose as acceptor, an initial genetically modified cell, preferably *E. coli*, having a recombinant gene that encodes an α-1,3-fucosyl transferase capable of fucosylating lactose, and separating 3-FL from said cell, from said culture medium or from both.

Yet another embodiment of the invention relates to preparing LNnT by a method comprising:
(i) obtaining a genetically modified *E. coli* cell that comprises a recombinant gene encoding a β-1,4-galactosyl transferase; and
(ii) culturing said cell on a carbon-based substrate in the presence of exogenous lacto-N-triose under conditions inducing its internalization by the cell and the production of LNnT by the cell.

According to another preferred embodiment of the invention, it is provided a method for making LNT comprising:
(i) obtaining a genetically modified *E. coli* cell that comprises a recombinant gene encoding a β-1,3-galactosyl transferase; and
(ii) culturing said cell on a carbon-based substrate in the presence of exogenous lacto-N-triose under conditions inducing its internalization by the cell and the production of LNT by the cell.

In both preferred embodiment in producing LNnT and LNT, the methods comprise a preliminary step of making lacto-N-triose by:
culturing, in an initial culture medium containing exogenously added lactose as acceptor, an initial genetically modified cell, preferably *E. coli*, having a recombinant gene that encodes an β-1,3-N-acetyl-glucosaminyl transferase capable of N-acetyl-glucosaminylating lactose, and separating lacto-N-triose from said initial cell, from said initial culture medium or from both.

The two-step fermentative production of LNnT and LNT as described above is beneficial because the formation of overglycosylated hexa- and octasaccharides are avoidable.

Other features of the invention will become apparent in view of the following exemplary embodiments which are illustrative but not limiting of the invention.

EXAMPLES

Bacterial Strains and Inoculum Preparation:

Engineered *E. coli* used for fucosylation was constructed from *E. coli* K strain in accordance with WO 01/04341 and Drouillard et al. *Angew. Chem. Int. Ed. Eng.* 45, 1778 (2006), by deleting genes that are liable to degrade the acceptor, the oligosaccharide product and its metabolic intermediates, inter alia the lacZ, lacA and wcaJ genes, maintaining man B, manC, gmd and wcaG genes involved in the GDP-fucose biosynthesis, and inserting *H. pylori* futC gene for α-1,2-fucosyl transferase.

General Fermentation Procedure:

The culture was carried out in a 3 l fermenter containing 1.5 l of mineral culture medium (Samain et al. *J. Biotechnol.* 72, 33 (1999)). The temperature was kept at 33° C. and the pH regulated at 6.8 with 28% $NH_4OH$. The inoculum (1% of the volume of the basal medium) consisted in a LB medium and the culture of the producing strain. The exponential growth phase started with the inoculation and stopped until exhaustion of the carbon source (glucose 17.5 g/l) initially added to the medium. The trisaccharide acceptor (various amount, given in the examples) and the inducer (isopropyl thio-β-D-galactopyranoside, IPTG, 1-2 ml of a 50 mg/ml solution) was added at the end of the exponential phase. Then a fed-batch was realized, using a 500 g/l aqueous glycerol solution, with a high substrate feeding rate of 4.5 g/h of glycerol for 1 l of culture for 5-6 hours followed by a lower glycerol feeding rate of 3 g/h for 1 l culture for a time indicated in the examples.

Purification:

At the end of the fermentation, the culture was centrifuged for 25-40 min at 4500-6000 rpm at 20-25° C. The supernatant was kept and acidify to pH 3 using a $H^+$ form resin. This resulted in the precipitation of the proteins. The resin was recovered by decantation and precipitated proteins removed by centrifugation for 25-40 min at 4500-6000 rpm at 20-25° C. The supernatant was passed through a $H^+$ form ion-exchange resin column and immediately neutralized by passing through a free base form anion exchange resin column. The compounds were eluted with water or aqueous ethanol, the flow rate was about 20 ml/min and the final pH was 6.0. The fractions containing the product were collected, concentrated and freeze-dried/crystallized/precipitated.

General LC-MS Conditions:

Instrument: Bruker microQTof II MS coupled with Dionex Ultimate 3000 UHPLC

Ionization: ESI negative

Dry temperature: 200° C.

Mode: LC-MS, 1:1 split of flow

Calibration: with Na-format cluster solution

Example 1

Production of DFL from 2'-FL

The fermentation was conducted according to the general procedure. At the end of the exponential phase a concentrated aqueous solution of 2'-FL was injected to the fermentation broth and the culturing was continued for 4 days. HPLC analysis showed that almost all 2'-FL was converted to a new compound (ratio: 8:92), that proved to be difucosyllactose according to LC-MS and NMR analysis. $^1H$ and $^{13}C$ resonances of DFL were assigned based on detailed analysis of standard one-($^1H$, $^{13}C$) and two-dimensional homo- and heterocorrelation (gDQCOSY, 2D-TOCSY, 2DNOESY, $^1H$—$^{13}C$ gHSQCAD, $^1H$—$^{13}C$ gHMBCAD) measurements. The spectral data (see Table 2) were in agreement within experimental error with those reported in the literature (Ishizuka et al. *J. Carbohydr. Chem.* 18, 523 (1999)).

TABLE 2

$^1$H and $^{13}$C resonance assignments for DFL in $D_2O$, 25° C. at 400 MHz($\alpha/\beta$ ratio is 9/11)

| Ring | proton | δ (ppm) | multiplicity | J (Hz) | Carbon | δ (ppm) |
|---|---|---|---|---|---|---|
| Glucose-α (glu) | H-1 | 5.18 | d | 3.8 | C-1 | 94.8 |
| | H-2 | 3.78 | m | | C-2 | 75.5 |
| | H-3 | 3.92 | m | | C-3 | 77.5 |
| | H-4 | 3.86 | m | | C-4 | 75.3 |
| | H-5 | 3.92 | m | | C-5 | 73.5 |
| | H-6x | 3.92 | m | | C-6 | 62.5 |
| | H-6y | 3.84 | m | | | |
| Glucose-β (glu) | H-1 | 4.62 | d | 8.1 | C-1 | 98.7 |
| | H-2 | 3.49 | dd | 9.5, 8.1 | C-2 | 78.3 |
| | H-3 | 3.71 | m | | C-3 | 79.8 |
| | H-4 | 3.88 | m | | C-4 | 75.4 |
| | H-5 | 3.46 | m | | C-5 | 78.3 |
| | H-6x | 3.99 | m | | C-6 | 62.6 |
| | H-6y | 3.80 | m | | | |
| Fucose-a, connected to α glucose (fu-a) | H-1 | 5.40 | d | 4.0 | C-1 | 101.1 |
| | H-2 | 3.80 | m | | C-2 | 70.8 |
| | H-3 | 3.98 | m | | C-3 | 72.0 |
| | H-4 | 3.81 | m | | C-4 | 74.7 |
| | H-5 | 4.86 | q | 6.3 | C-5 | 69.3 |
| | $CH_3$ | 1.24 | d | 6.3 | $CH_3$ | 18.1 |
| Fucose-a connected to β glucose (fu-a) | H-1 | 5.45 | d | 4.0 | C-1 | 101.0 |
| | H-2 | 3.80 | m | | C-2 | 70.8 |
| | H-3 | 3.98 | m | | C-3 | 71.9 |
| | H-4 | 3.80 | m | | C-4 | 74.7 |
| | H-5 | 4.87 | q | 6.3 | C-5 | 69.3 |
| | $CH_3$ | 1.24 | d | 6.3 | $CH_3$ | 18.1 |
| Galactose (ga) | H-1 | 4.49 | d | 7.9 | C-1 | 102.9 |
| | H-2 | 3.63 | m | | C-2 | 79.1 |
| | H-3 | 3.85 | m | | C-3 | 76.3 |
| | H-4 | 3.87 | m | | C-4 | 71.5 |
| | H-5 | 3.59 | m | | C-5 | 77.6 |
| | H-6x | 3.75 | m | | C-6 | 64.2 |
| | H-6y | 3.71 | m | | | |
| Fucose-b (fu-b) | H-1 | 5.28 | d | 3.3 | C-1 | 102.1 |
| | H-2 | 3.81 | m | | C-2 | 70.8 |
| | H-3 | 3.78 (3.76) | m | | C-3 | 72.4 |
| | H-4 | 3.82 | m | | C-4 | 74.4 |
| | H-5 | 4.29 (4.27) | q | 6.3 | C-5 | 69.6 |
| | $CH_3$ | 1.26 | d | 6.3 | $CH_3$ | 18.2 |

The invention claimed is:

1. A method for producing difucosyllactose, said method comprising the step of culturing, in a culture medium containing an exogenously added acceptor and a genetically modified *E. coli* of LacY$^+$ genotype having a *H. pylori* futC gene that encodes an α-1,2-fucosyl transferase that is (a) capable of modifying said acceptor and (b) is necessary for the synthesis of said difucosyllactose from said acceptor wherein the acceptor consists of 2′-O-fucosyllactose.

2. The method according to claim 1, comprising the steps of:
   (i) obtaining said *E. coli*, and
   (ii) culturing said *E. coli* in a carbon-based substrate containing culture medium in the presence of said acceptor to internalize it in said *E. coli* and to produce said difucosyllactose.

3. The method according to claim 1 further comprising the step of separating said difucosyllactose from said *E. coli*, from said culture medium or from both.

4. The method according to claim 1, wherein said α-1,2-fucosyl transferase is an enzyme capable of performing a fucosylation, by transferring a fucosyl residue of an activated fucose nucleotide to the acceptor, wherein the activated fucose nucleotide is produced by a de novo pathway by said *E. coli*.

5. The method according to claim 1, wherein said culturing comprises:
   (a) a first phase of exponential cell growth ensured by a carbon-based substrate, and
   (b) a second phase of cell growth limited by a carbon-based substrate which is added continuously.

6. The method according to claim 5, wherein said carbon-based substrate is selected from the group consisting of glycerol and glucose.

7. The method according to claim 1, further comprising the addition of an inducer to said culture medium to induce the expression in said *E. coli* of said α-1,2-fucosyl transferase and/or of a protein involved in active transport of the acceptor.

8. The method according to claim 7, wherein said inducer is isopropyl β-D-thiogalactoside (IPTG).

9. The method according to claim 1, wherein said method further comprises the preliminary steps of making 2′-O fucosyllactose comprising:
   culturing, in a separate culture medium containing exogenously added lactose as acceptor, said genetically modified *E. coli* cell, and
   separating 2′-O fucosyllactose from said cell, from said culture medium or from both.

10. The method according to claim 1, wherein said genetically modified *E. coli* cell has a LacZ$^-$Y$^+$ genotype.

* * * * *